United States Patent [19]

Turley

[11] Patent Number: 4,892,543
[45] Date of Patent: Jan. 9, 1990

[54] INTRAOCULAR LENS PROVIDING ACCOMODATION

[76] Inventor: Dana F. Turley, 4651 Prices Creek Rd., Huntington, W. Va. 25701

[21] Appl. No.: 305,603

[22] Filed: Feb. 2, 1989

[51] Int. Cl.$^4$ .............................................. A61F 2/16
[52] U.S. Cl. ......................................................... 623/6
[58] Field of Search ............................................. 623/6

[56] References Cited

U.S. PATENT DOCUMENTS

| 4,253,199 | 3/1981 | Banko | 623/6 |
|---|---|---|---|
| 4,373,218 | 2/1983 | Schachar | 623/6 |
| 4,409,691 | 10/1983 | Levy | 623/6 |
| 4,731,078 | 3/1988 | Stoy et al. | 623/6 |

Primary Examiner—Ronald L. Frinks
Attorney, Agent, or Firm—Nies, Webner, Kurz & Bergert

[57] ABSTRACT

An intraocular lens that provides accommodation in direct response to contraction and relaxation of the ciliary body. The lens includes a first component having fixed refractive power and a second component having varying refractive power, the components being relatively movable towards each other as the ciliary body contracts to increase the total refractive power of the lens.

14 Claims, 2 Drawing Sheets

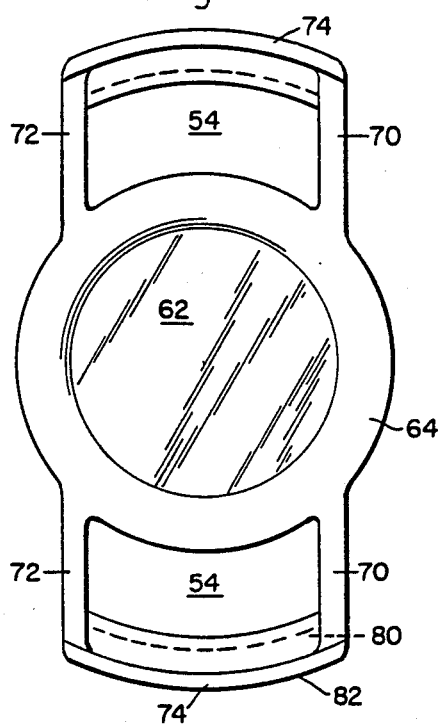
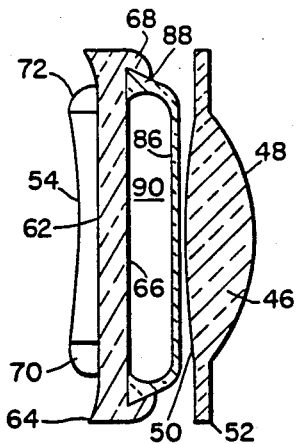
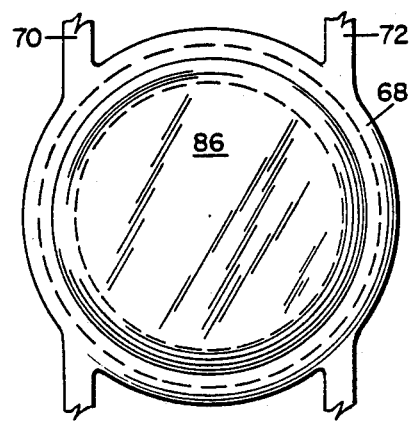
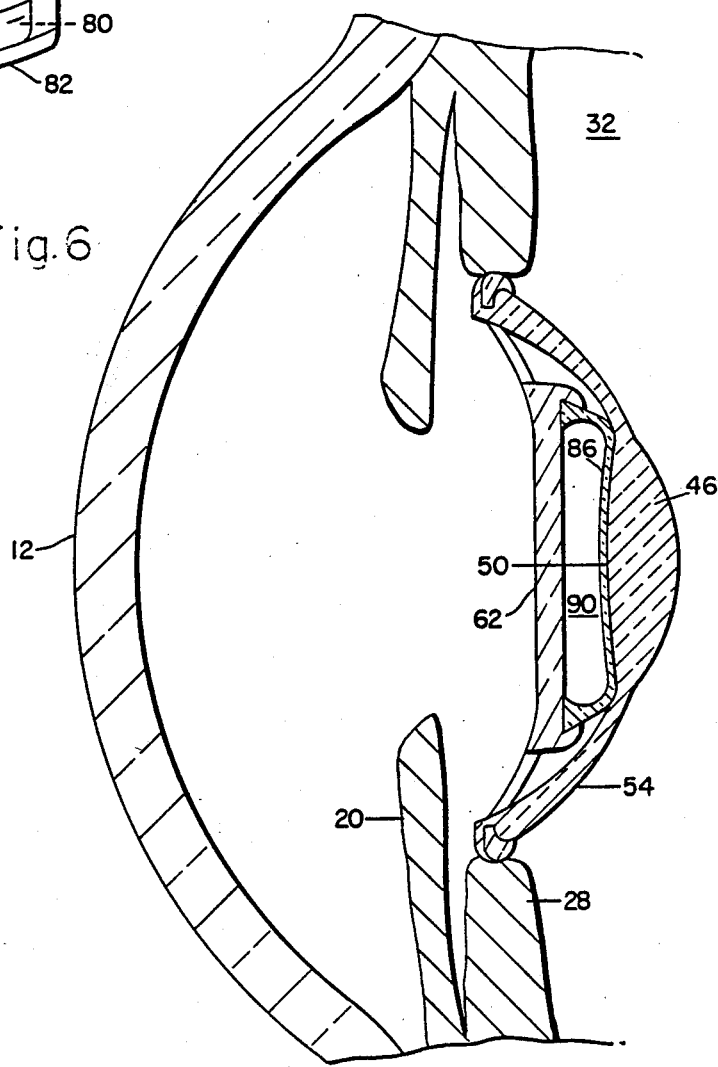

INTRAOCULAR LENS PROVIDING ACCOMODATION

BACKGROUND OF THE INVENTION

This invention relates generally to artificial intraocular lens for replacing the natural lens of the eye, and more particularly to a novel intraocular lens which is capable of emulating the natural process of accommodation in direct response to contraction and relaxation of the ciliary body of the host eye.

Accommodation is the natural process by which the lens of the eye can sharpen the curvature of its front and back surfaces and thereby change its refractive power in order to adjust from distance vision to near vision. This occurs in response to contraction of the ciliary body which results in an approximate one-half millimeter decrease in the equatorial diameter of the lens capsule. A recent article, "How the Human Eye Focuses" appearing in the July, 1988 issue of the magazine *Scientific American*, describes very well the structure of the eye and the accommodation process.

Most conventional intraocular lenses have a predetermined fixed refractive power with no accommodation capability. Prior proposals intended to provide the accommodation function are illustrated in U.S. Pat. Nos. 4,373,218, 4,409,691, and 4,731,078, but these are rather complicated in construction and operation.

In addition, conventional intraocular lenses exhibit positioning instability in the eye, called decentration. These lenses decenter because the haptic fingers which support the lens from the ciliary body or lens capsule have very small surface areas in contact with these tissues. Small surface areas greatly increase pressure of the fingers against these tissues, thus making it difficult to maintain the lens in its centered position.

Another problem associated with conventional intraocular lenses is the introduction of significant amounts of glare or halo effects around images, especially in dim lighting situations when the pupillary aperture is large.

SUMMARY OF THE INVENTION

Accordingly, a primary object of this invention is to provide a novel simplified intraocular lens capable of emulating the natural process of accommodation.

Another object of the invention is to provide the novel intraocular lens, wherein accommodation occurs over a substantial variable range of refractive power change.

Still another object of this invention is to provide the above novel intraocular lens which includes a first optical component having a fixed refractive power and a second optical component having a variable refractive power, the components being relatively movable towards each other in response to contraction of the ciliary body to increase the refractive power of the lens.

Another object of the invention is to provide the above novel intraocular lens which functions as a mechanical optical transducer capable of converting small dimensional changes of the ciliary body of the eye into large refractive power changes.

A further object of the invention is to provide the above novel intraocular lens wherein the first optical component has a surface of predetermined configuration for engagement by a flexible membrane of the second component, the refractive power of the second component gradually increasing as the membrane conforms to the shape of that surface.

Another object of the invention is to provide the above novel lens wherein the first and second optical components are connected together by haptic arms or fingers of substantial width and surface area to stabilize the lens as mounted within the ciliary body and eliminate decentration.

A further object of the invention is to provide the above novel intraocular lens wherein the haptic arms are shaped so as to create an outer optical zone around a primary central optical zone, the outer zone diverging light away from the principal axis and thereby reducing glare and halo around images.

Another object of the invention is to provide the above novel intraocular lens wherein the first optical component will continue to function should the second optical component fail or be destroyed, the lens thereby affording a special safety feature.

Other objects and advantages will become apparent as the description proceeds in connection with the accompanying drawings.

BRIEF DESCRIPTION OF THE DRAWINGS

FIG. 3 is a view taken generally along line 3—3 of FIG. 2;

FIG. 4 is a fragmentary sectional view taken along line 4—4 of FIG. 2;

FIG. 5 is a fragmentary view taken along line 5—5 of FIG. 2; and

FIG. 6 is a view similar to FIG. 2, but illustrating the maximum refractive power position of the fixed and variable optical components for near vision in respense to contraction of the ciliary body.

DETAILED DESCRIPTION OF THE INVENTION

Figure 1:
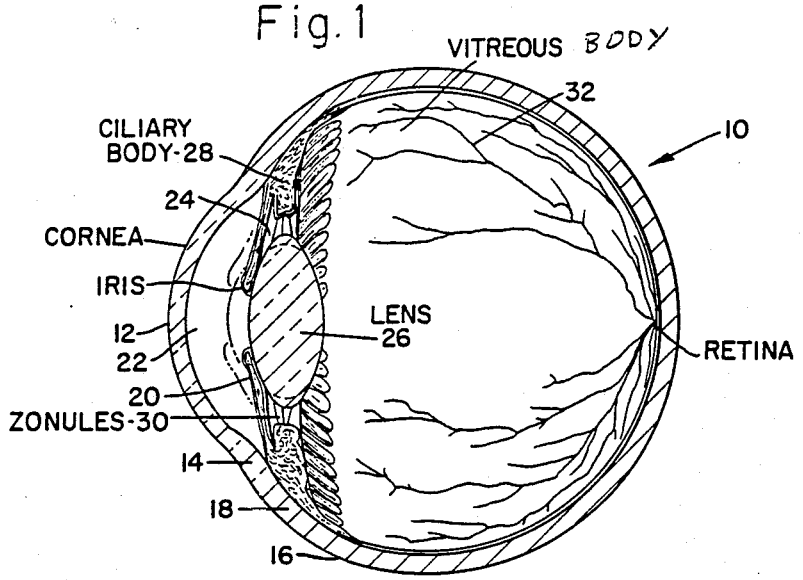
FIG. 1 is a longitudinal fragmentary section through a human eye.

As shown in FIG. 1, the human eye 10 includes cornea 12, limbus 14, sclera 16, conjunctive 18, iris 20, anterior chamber 22, posterior chamber 24, natural lens 26, ciliary muscle or body 28, zonules 30, and vitreous body 32. Chambers 22 and 24 are filled with a fluid known as the aqueous humor.

When the eye is focused at a distance, the ciliary muscle or body 28 relaxes and expands, and its diameter is at a maximum. As muscle 28 expands it pulls zonules 30 taut, causing them in turn to pull on lens 26. The pulling flattens the front and back of the lens and increases the diameter of its equator. In this condition - called the unaccommodated state - the ability of the lens to bend light is at a minimum.

When the eye attempts to focus on a point closer than e.g. 20 feet away, the ciliary muscle contracts, reducing the diameter of its opening and also causing the muscle to move slightly forward. Both changes reduce the stress on the zonules and thereby lessen the stress exerted by the zonules on the lens. The lens thereupon undergoes elastic recovery and the lens rebounds to a more relaxed state. As the lens focuses on progressively closer objects, it becomes thicker from front to back, its surface become more sharply curved and the diameter of the equator shrinks (as shown in phantom in FIG. 1). This relaxation process is precisely controlled to provide the exact degree of extra refractive power needed for focusing on objects closer than 20 feet away.

The lens, then, is unaccommodated - flattest and the least refractive - when it is under maximum stress: when the eye focuses at a distance and the ciliary muscle is totally relaxed. The lens is maximally accommodated - most sharply curved and most refractive - when it is under the least stress: when the eye focuses on the closest discernible object and the ciliary muscle is fully contracted.

Referring to FIGS. 2-5, the novel intraocular lens 40 of the invention is implanted in the posterior chamber 24 of the host eye and is constructed of conventional transparent optical materials such as PMMA (polymethylmethacrylates), HEMA (hydroxyethylmethacrylates), and silicone elastomers (polydimethylsiloxanes).

Lens 40 comprises a first optical component 42 having a substantially fixed refractive power and a second optical component 44 having a variable refractive power. Component 42 includes a main solid central lens element 46 having a rear spherical surface 48 seated within vitreous body 32, the radius of surface 48 varying for each patient and providing a fixed refractive power which is estimated to correct the refractive power deficiency induced by aphakia in the host eye of the patient. For example, surface 48 may have a refractive power of 30 diopter in a worst case situation.

Element 46 also has a forward convex spherical surface 50 of a predetermined radius, the surface 50 acting as a contour gauge or template which sets and controls the quality, range and rate of refractive power change in variable component 44 in a manner to be described.

A spherical ring 52 surrounds element 46 and a pair of flexible haptic arms 54 curve outwardly and forwardly from ring 52 and have a substantial width about equal to the diameter of element 46. Each arm has a forward concave surface 56 having a radius of about 6.0 mm and a rearward concave surface 58 having a somewhat greater radius of about 7.5 mm.

Variable component 44 includes a rigid central element 60 having a flat forward circular surface 62 of about 5mm diameter surrounded by a concave peripheral ring section 64, and a flat circular rear surface 66 bordered by a peripheral flange 68. A pair of spaced flexible haptic fingers 70 and 72 curve outwardly and forwardly from ring section 64 at opposite sides thereof, and join at their outer ends a circumferential segment 74. Each finger has a curved front surface 76 of a radius of about 15 mm and a rear surface 78 of a somewhat greater radius of about 15.20 mm.

Figure 2:
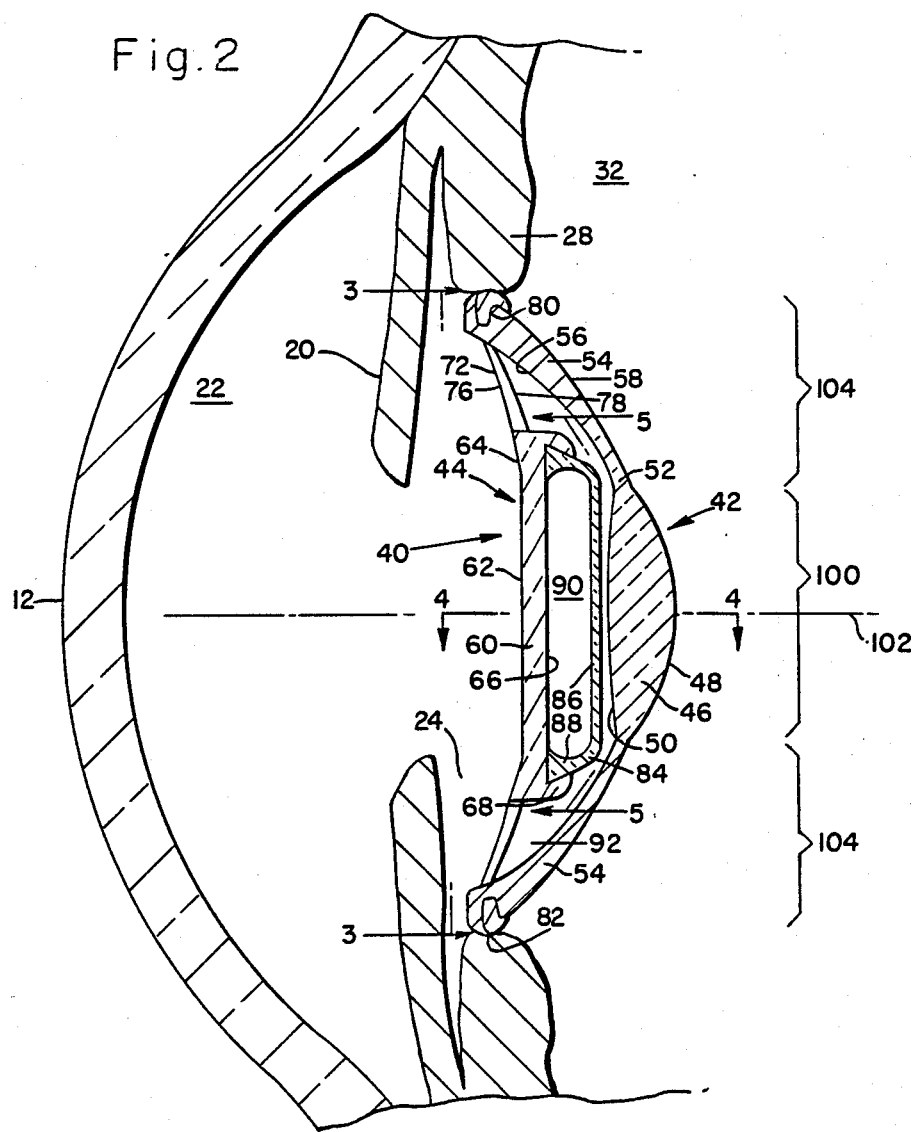
FIG. 2 is a fragmentary sectional view illustrating the novel intraocular lens of the invention magnified about nine times actual size, the fixed and variable optical components being positioned for far vision in response to relaxation of the ciliary body.

As shown best in FIGS. 2 and 3, the outer edges of arms 54 of component 42 fit between fingers 70 and 72 and interlock with segment 74 via a tongue and groove like connection 80. Each outer circumferential edge or rim 82 is smoothly radiused and provides a substantial surface area engaging and seating within ciliary body 28.

Component 44 also includes a thin pliable optical element 84 having a normally flat rear flexible membrane 86 and a generally forwardly extending cylindrical wall 88 which snaps into interlocking engagement with flange 68. Element 84 together with surface 66 define a chamber 90 containing a compressive gaseous fluid, such as air, which functions as an optical element having a low refractive index.

The space or chamber 92 between components 42 and 44 will be filled with the aqueous humor of the host eye.

From the description thus far, it is seen that several optical elements function within lens system 40 including from fixed component 42 element 46 and its arms 54, and from variable component 44 element 60 and its fingers 70 and 72, the air in chamber 90, membrane 84, and the aqueous humor within chamber 92.

In addition as shown in FIG. 2, two coaxial optical zones exist within the system, a first cylindrical central zone 100 about 5mm in diameter formed about the principal axis 102 and converging light at the fovea of the retina, and a second outer cylindrical distal zone 104 surrounding zone 100 and diffracting light away from the principal axis to eliminate glare.

Lens 40 is implanted as shown in FIG. 2 with rims 82 in contact with ciliary body 28, or alternatively in contact with the walls of the capsule of the natural lens when the capsule is not removed. As shown in FIG. 3 rims 82 extend through a substantial arcuate length to provide a smooth, substantial surface area of contact which greatly stabilizes and maintains the lens in its centered position. As mounted, the lens will respond directly to forces imposed on rims 82 by the contraction and relaxation of ciliary body 28. The lens acts as a mechanical optical transducer, converting small dimensional changes of the ciliary body into large refractive power changes.

In FIG. 2, ciliary body 28 is in its relaxed or expanded condition and the host eye is focused for distance viewing. Components 42 and 44 are positioned as shown with membrane 86 in its flattened condition, spaced about 0.15 mm from template surface 50. Thus, the total refractive power of lens 40 equals the fixed refractive power provided by element 46 and surface 48, e.g. 30 diopters, since the optical flats 62, 66, 90 and 86 merely act as windows.

When the host eye starts to focus on close objects, during accommodation ciliary body 28 contracts and applies compressive pressure against rims 82 in a direction perpendicular to axis 102 which causes flexing of arms 54 and fingers 70, 72 and vaulting or displacement of components 42 and 44 in a direction along axis 102 rearwardly away from iris 20. Because the radius of curvature of fingers 70 and 72 is greater than the radius of curvature of arms 54, element 60 is displaced along axis 102 at a greater rate than element 46. After about 0.125 mm compression on each rim 82 (total diameter decrease of 0.25 mm) membrane 86 engages and gradually conforms to the convex template surface 50, causing a gradual increase of refractive power. Accommodation continues until membrane 86 conforms fully to surface 50 as shown in FIG. 6.

At any position of accomodation, the new contour of high refractive index optical elements membrane 86 and aqueous humor between membrane 86 and surface 50 against the low refractive index optical element air within chamber 90 causes an increase of refractive power within zone 102. For example, providing surface 50 with a radius of about 20.0 mm will enable variable component 44 to produce a gradual increase of refractive power up to a maximum 14 diopters when positioned as in FIG. 6.

Thus, lens 40 provides a continuously variable range of refractive power defined at its lowest end (with the components positioned as in FIG. 2) by the diopter value of fixed component surface 48, e.g. 30 diopters, and at its highest end (with the components positioned as in FIG. 6) by the sum of the diopter value of surface 48 plus the maximum 14 diopter increase from component 44, e.g. 44 diopters.

When the host eye refocuses on distant objects ciliary body 28 relaxes and expands, and the compressive spring forces within arms 54 and fingers 70 and 72 cause components 40 and 42 to return to the distance viewing position of FIG. 2.

It should be noted that should membrane 86 fail or be damaged, e.g. by a necessary subsequent surgical procedure such as a YAG laser capsulotomy, causing component 44 to discontinue its accommodation, fixed component 42 continues to function and provide the fixed refractive power of surface 48. Removal of lens 40 is not required. This is an important safety feature of the lens.

It should also be understood that light impinging on surface 62 and entering zone 100 is converged along principal axis 102 on the fovea of the retina of the host eye. Light outside surface 62 inpinging on rim 64, arms 54, and fingers 70 and 72 within zone 104 is diffracted away from axis 102 to eliminate glare.

While components 42 and 44 have been illustrated as separate pieces, it is anticipated that they may be molded together to form lens 40 as one piece. Also it is possible that a fluid other than air may be contained within chamber 90.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. An intraocular lens for mounting within the ciliary body of a host eye and capable of emulating the natural process of accommodation comprising first optical means having a first refractive power, second optical means having a variable refractive power, said first and second optical means being connected together for relative movement along the principal axis of lens, said first optical means including a surface of predetermined configuration engageable by said second optical means upon relative movement of said first and second optical means towards each other in response to contraction of the ciliary body to increase the refractive power of the lens.

2. The intraocular lens of claim 1, said first optical means having a substantially fixed refractive power.

3. The intraocular lens of claims 1 or 2, said first and second optical means having a central zone which converges light toward said principal axis and an outer distal zone which diffracts light away from said principal axis.

4. The intraocular lens of claim 3, said first and second optical means including central optical elements located within said central zone and flexible mounting means extending radially outwardly from said central elements within said distal zone, the mounting means being shaped to diffract light away from the principal axis.

5. The intraocular lens of claim 4, wherein the mounting means are connected together and permit relative axial movement between said first and second optical means.

6. The intraocular lens of claim 5, wherein said mounting means extend a substantial circumferential distance around said optical means and provide substantial support within the ciliary body.

7. The intraocular lens of claims 1 or 2, said second optical means including a flexible optical element which increases in refractive power as it engages with and conforms to said surface during the accommodation process.

8. An intraocular lens for mounting within the ciliary body of a host eye comprising first optical means having a substantially fixed refractive power, second optical means including a flexible optical means providing a variable refractive power, said first and second optical means being connected together in substantial coaxial alignment for relative movement along the principal axis of the lens, said first optical means including a surface of predetermined configuration engageable by said flexible optical means upon relative movement of said first and second optical means towards each other in direct response to contraction of the ciliary body, the refractive power of said flexible optical means gradually increasing as it increasingly conforms to said surface, whereby said second optical means provides a continuously variable range of refractive power during the accommodation process.

9. The intraocular lens of claim 8, said first and second optical means having a central zone which converges light toward said principal axis and an outer distal zone which diffracts light away from said principal axis.

10. The intraocular lens of claim 9, said first and second optical means comprising central optical elements including said flexible optical means and said surface located within said central zone and flexible mounting means extending radially outwardly from said central elements within said distal zone, the mounting means being shaped to diffract light away from the principal axis.

11. The intraocular lens of claim 10, wherein the mounting means are connected together and permit relative axial movement between said first and second optical means.

12. The intraocular lens of claim 11, wherein said mounting means extend a substantial circumferential distance around said optical means and provide substantial support within the ciliary body.

13. The intraocular lens of claim 8, said flexible optical means comprising a substantially rigid optical element, a flexible optical element connected to and spaced from said rigid element and defining a fluid chamber therewith, said flexible optical element engaging with and conforming to said surface.

14. The intraocular lens of claim 13, wherein air is contained within said chamber.

* * * * *